United States Patent
Akiyama et al.

(10) Patent No.: US 7,910,316 B2
(45) Date of Patent: Mar. 22, 2011

(54) KIT AND METHOD FOR DETECTING UROTHELIAL CANCER

(75) Inventors: Hideo Akiyama, Kanagawa (JP); Yoshinori Tanaka, Kanagawa (JP); Satoko Kozono, Kanagawa (JP); Hitoshi Nobumasa, Shiga (JP); Osamu Ogawa, Kyoto (JP); Takeshi Takahashi, Kyoto (JP)

(73) Assignees: Toray Industries, Inc., Tokyo (JP); Kyoto University, Kyoto (JP)

( * ) Notice: Subject to any disclaimer, the term of this patent is extended or adjusted under 35 U.S.C. 154(b) by 248 days.

(21) Appl. No.: 11/991,184

(22) PCT Filed: Sep. 1, 2006

(86) PCT No.: PCT/JP2006/317379
§ 371 (c)(1),
(2), (4) Date: Feb. 28, 2008

(87) PCT Pub. No.: WO2007/026895
PCT Pub. Date: Mar. 8, 2007

(65) Prior Publication Data
US 2010/0009347 A1    Jan. 14, 2010

(30) Foreign Application Priority Data
Sep. 2, 2005 (JP) .................................. 2005-255370

(51) Int. Cl.
*G01N 33/53* (2006.01)
*C12Q 1/68* (2006.01)

(52) U.S. Cl. ............................................ 435/7.1; 435/6

(58) Field of Classification Search .................. None
See application file for complete search history.

(56) References Cited

FOREIGN PATENT DOCUMENTS
WO  WO-2004/108899 A2  12/2004
WO  WO-2004/112589 A2  12/2004
WO  WO-2005/044990 A2  5/2005

OTHER PUBLICATIONS

Tadros et al (Journal of Endourology; Jun. 2003, 17(5): 333-336).*
Tockman et al (Cancer Res., 1992, 52:2711s-2718s).*
Druzgal et al (Head & Neck, 2005, 771-784).*
Tadros et al (Journal of Endourology, 2003, 17(5): 333-336).*
Igarashi et al., "Jingan ni okeru IL-8/GROα mRNA no Hatsugen," Biotherapy, vol. 12, No. 5, 1998, pp. 632-634.
Tadros et al., "In vivo proteomic analysis of cytokine expression in laser capture-microdissected urothelial cells of obstructed ureteropelvic junction procured by laparoscopic dismembered pyeloplasty," Journal of endourology, vol. 17, No. 5, 2003, pp. 333-336.
Strausberg et al., "*Homo sapiens* chemokine (C-X-C motif) ligand 1 (melanoma clone MGC:9049 Image:3856841), complete cds," Accession BC011976, Version BC011976.1, GI:15080461, 2006.
Kawanishi et al., "Saibo Baiyo Josei no Proteome Kaiseki ni yoru Nyoro Johi Saibo Zoshoku Inshi no Dotei," Annual Meeting of the Japan Cancer Association Kiji, 2005, pp. 292.
Mueller et al., "Melanoma growth stimulatory activity enhances the phosphorylation of the class II interleukin-8 receptor in non-hematopoietic cells," The Journal of Biological Chemistry, vol. 269, No. 3, 1994, pp. 1973-1980.
Alexandroff et al., "Role for CD40-CD40 ligand interactions in the immune response to solid tumours," Molecular Immunology, vol. 37, No. 9, 2000, pp. 515-526.
Tachibana, "Cytokine to Gan no Zoshoku," Human Cell, vol. 8, No. 4, 1996, pp. 215-216.
Peterson et al., "The Innate Immune System Is Activated by Stimulation of Vaginal Epithelial Cells with *Staphylococcus aureus* and Toxic Shock Syndrome Toxin 1," Infection and Immunity, vol. 73, No. 4, 2005, pp. 2164-2174.

* cited by examiner

*Primary Examiner* — Sean E Aeder
(74) *Attorney, Agent, or Firm* — Birch, Stewart, Kolasch and Birch, LLP

(57) ABSTRACT

This invention relates to a method for detecting in vitro a urothelial cancer, comprising measuring CXCL1 protein, or expression of a gene encoding the protein, in a biological sample from a subject, and to a kit for diagnosing a urothelial cancer comprising an antibody or nucleic acid probe, which is capable of binding specifically to the CXCL1 protein or a gene encoding the protein, respectively.

17 Claims, 5 Drawing Sheets

Marker     Benign cell     Bladder cancer-derived cell #5637     Bladder cancer-derived cell #T24

SEQUENCE LISTING

```
<160> NUMBER OF SEQ ID NOS: 2

<210> SEQ ID NO 1
<211> LENGTH: 1103
<212> TYPE: DNA
<213> ORGANISM: Homo sapiens

<400> SEQUENCE: 1
cacagagccc gggccgcagg cacctcctcg ccagctcttc cgctcctctc acagccgcca      60
gacccgcctg ctgagcccca tggcccgcgc tgctctctcc gccgccccca gcaatccccg     120
gctcctgcga gtggcactgc tgctcctgct cctggtagcc gctggccggc gcgcagcagg     180
agcgtccgtg gccactgaac tgcgctgcca gtgcttgcag accctgcagg gaattcaccc     240
caagaacatc caaagtgtga acgtgaagtc ccccggaccc cactgcgccc aaaccgaagt     300
catagccaca ctcaagaatg ggcggaaagc ttgcctcaat cctgcatccc ccatagttaa     360
gaaaatcatc gaaaagatgc tgaacagtga caaatccaac tgaccagaag ggaggaggaa     420
gctcactggt ggctgttcct gaaggaggcc ctgcccttat aggaacagaa gaggaaagag     480
agacacagct gcagaggcca cctggattgt gcctaatgtg tttgagcatc gcttaggaga     540
agtcttctat ttatttattt attcattagt tttgaagatt ctatgttaat attttaggtg     600 taaataatt aagggtatga ttaactctac ctgcacactg tcctattata ttcattcttt      660
ttgaaatgtc aaccccaagt tagttcaatc tggattcata tttaatttga aggtagaatg     720
ttttcaaatg ttctccagtc attatgttaa tatttctgag gagcctgcaa catgccagcc     780
actgtgatag aggctggcgg atccaagcaa atggccaatg agatcattgt gaaggcaggg     840
gaatgtatgt gcacatctgt tttgtaactg tttagatgaa tgtcagttgt tatttattga     900
aatgatttca cagtgtgtgg tcaacatttc tcatgttgaa actttaagaa ctaaaatgtt     960
ctaaatatcc cttggacatt ttatgtcttt cttgtaaggc atactgcctt gtttaatggt    1020
agttttacag tgtttctggc ttagaacaaa ggggcttaat tattgatgtt ttcatagaga    1080
atataaaaat aaagcactta tag                                            1103

<210> SEQ ID NO 2
<211> LENGTH: 107
```

```
<212> TYPE: PRT
<213> ORGANISM: Homo sapiens

<400> SEQUENCE: 2

Met Ala Arg Ala Ala Leu Ser Ala Ala Pro Ser Asn Pro Arg Leu Leu
1               5                   10                  15

Arg Val Ala Leu Leu Leu Leu Leu Val Ala Ala Gly Arg Arg Ala
            20                  25                  30

Ala Gly Ala Ser Val Ala Thr Glu Leu Arg Cys Gln Cys Leu Gln Thr
        35                  40                  45

Leu Gln Gly Ile His Pro Lys Asn Ile Gln Ser Val Asn Val Lys Ser
    50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
                100                 105
```

US 7,910,316 B2

KIT AND METHOD FOR DETECTING UROTHELIAL CANCER

FIELD OF THE INVENTION

The present invention relates to a method for detecting a urothelial cancer comprising measuring CXCL1 protein, or expression of a gene encoding the protein, which is useful for detecting or diagnosing the urothelial cancer.

The present invention also relates to a kit for diagnosing or detecting a urothelial cancer, which comprises a substance capable of binding to the CXCL1 protein or a gene encoding the protein.

BACKGROUND OF THE INVENTION

The "urothelial cancer" is a collective name for bladder cancer, renal pelvis cancer, urinary duct cancer, and the like. Such cancers are caused by canceration of a transitional epithelium cell of the urinary tract, and their properties are considered to be common or shared. The number of patients suffered from urothelial cancer is the second-highest among patients with urogenital cancers, following prostate cancer. According to the "Population Survey Report" provided in 2001 by the Statistics and Information Department at the Ministry of Health, Labour and Welfare of Japan, the number of patients with bladder cancer was as many as 9,765 for males and 3,243 for females, and the number of patients died of bladder cancer was 3,459 for males and 1,587 for females, annually in Japan. By contrast, the number of patients with renal pelvis cancer or urinary duct cancer is considerably smaller than those with bladder cancer, and the numbers of patients died of these cancers were 797 and 713, respectively, in total of males and females.

Although there are no studies on prevention of bladder cancer or any other urothelial cancer, the development of bladder cancer is often found in people in their 50's or older, and men are more likely to develop such cancer, at a rate 2 to 3 times higher than that for women. Also, smokers are approximately 4 times higher in the onset of bladder cancer than nonsmokers. Bladder cancer is roughly classified into two types: i.e., superficial bladder cancer and infiltrative bladder cancer. Superficial papillary tumors have relatively low malignancy and protrudes on the inner cavity of the bladder (i.e., the inner surface of the bladder), but the degree of infiltration is shallow, and the surface is papilliform (like a cauliflower) with thin stems. Such cancer can be treated endoscopically; however, it recurs in the bladders of half or more patients. The depth of cancer invasion may reach the submucosal level, although it would not reach the bladder's muscle layer. In contrast, infiltrative cancer is high in malignancy, the degree of invasion is deep, it tends to invade the deep portion of the bladder wall, and it may metastasize to other portions of the body. In order to treat infiltrative cancer, accordingly, treatment that imposes a burden on a patient's body, such as bladder extirpation, use of an anticancer agent, or radiation therapy, is required.

The most common symptom of bladder cancer is painless hematuria; however, the symptoms may be similar to those of cystitis, such as increased urinary frequency, pain during urination, or the feeling of incomplete emptying of the bladder. Diagnosis of bladder cancer is carried out via, for example, urine analysis (cytological diagnosis), X-ray photography, or endoscopic diagnosis. Due to a lack of specific and highly sensitive tumor markers that can be used for the blood or urine useful for early diagnosis, however, bladder cancer is often detected after the cancer has progressed. Urothelial cancer that develops at sites other than the bladder also has the same properties. Accordingly, practical application of a simple detection method with the use of specific and highly sensitive tumor markers for urothelial cancer, and particularly for bladder cancer, is desired.

A variety of markers and methods have been proposed for detection and determination of bladder cancer. Examples thereof include methods wherein bladder cancer is evaluated based on changes in expression levels of genes such as nucleophosmin/B23 (JP Patent Publication (kokai) No. 2004-337120 (A)), HURP (JP Patent Publication (kokai) No. 2004-248508 (A)), or CYP4B1 or CYP4B2 (JP Patent Publication (kokai) No. 2002-238599 (A)); a method wherein bladder cancer is evaluated based on the expression or amount of a given protein in a urine specimen (JP Patent Publication (kokai) Nos. 2004-61288 (A) and H7-309895 (1995)(A)); and a method wherein bladder cancer is evaluated using the concentration of soluble Fas in the blood as an indication (JP Patent Publication (kokai) No. 2000-131321 (A)).

DISCLOSURE OF THE INVENTION

Problems to be Solved by the Invention

The present invention is intended to discover a novel urothelial cancer tumor marker and to provide a method for effectively detecting a urothelial cancer, and particularly bladder cancer.

Means to Solve the Problems

We have conducted intensive studies in order to attain the above objects. As a result, we have now found that urothelial cancers could be significantly detected by using an antibody that can bind specifically to a tumor marker, i.e. CXCL1 protein, or alternatively a nucleic acid capable of attaching to a gene encoding the protein, a transcription product thereof, or cDNA thereof. This has led to the completion of the present invention.

SUMMARY OF THE INVENTION

Specifically, the present invention includes the following inventions.

(1) A method for detecting urothelial cancer comprising measuring CXCL1 protein, or the expression of a gene encoding the protein, in vitro in a biological sample from a subject.

(2) The method according to (1), wherein the amount of the protein or the expression level of the gene is measured.

(3) The method according to (1) or (2), wherein the significant increase in amount of the protein or in expression level of the gene relative to that of a control sample is used as an indication.

(4) The method according to (3), wherein the increase is at least 2 times.

(5) The method according to (3), wherein the increase is at least 3 times.

(6) The method according to any of (1) to (5), wherein the measurement is carried out by an immunological method.

(7) The method according to any of (1) to (5), wherein the measurement is carried out by hybridization.

(8) The method according to any of (1) to (7), wherein the measurement is carried out with the use of a substance capable of binding to the protein or gene.

(9) The method according to (8), wherein the substance capable of binding to the protein is an antibody or a fragment thereof.

(10) The method according to (8), wherein the substance capable of binding to the gene is a nucleic acid probe.

(11) The method according to (10), wherein the nucleic acid probe comprises a nucleic acid consisting of the nucleotide sequence as shown in SEQ ID NO: 1 or a mutant thereof, a nucleic acid consisting of a sequence complementary thereto, a nucleic acid hybridizing under stringent conditions to the nucleic acid, or a fragment comprising 15 or more continuous nucleotides thereof.

(12) The method according to any of (9) to (11), wherein the antibody or nucleic acid probe is labeled.

(13) The method according to any of (1) to (6), (8), (9), and (12), wherein the protein is measured immunologically in a sample using an antibody or fragment thereof, which binds specifically to the protein or a fragment thereof, thereby detecting a urothelial cancer using, as an indication, the increase in amount of the protein relative to that of a control sample.

(14) The method according to any of (1) to (5), (7), (8), and (10) to (12), wherein the expression level of the gene is measured in the sample using a probe, which is a nucleic acid consisting of the nucleotide sequence as shown in SEQ ID NO: 1 or a mutant thereof, a nucleic acid consisting of a sequence complementary thereto, a nucleic acid hybridizing under stringent conditions to the nucleic acid, or a fragment comprising 15 or more continuous nucleotides thereof, thereby detecting a urothelial cancer using, as an indication, the increase in expression level of the gene relative to that of a control sample.

(15) The method according to any of (1) to (14), wherein the urothelial cancer is selected from the group consisting of bladder cancer, renal pelvis cancer, urinary duct cancer, and urinary tract cancer.

(16) The method according to any of (1) to (15), wherein the sample is blood, plasma, serum, or urine.

(17) The method according to any of (1) to (15), wherein the sample is a urothelial tissue or cell.

(18) The method according to any of (1) to (6), (8), (9), (12), (13), and (15) to (17), wherein the protein has the amino acid sequence as shown in SEQ ID NO: 2 or a mutant thereof.

(19) The method according to any of (1) to (5), (7), (8), (10) to (12), and (14) to (17), wherein the gene has the nucleotide sequence as shown in SEQ ID NO: 1 or a mutant thereof.

(20) A kit for diagnosing a urothelial cancer comprising an antibody or fragment thereof, which binds specifically to the CXCL1 protein or a fragment thereof, or a chemically modified derivative of the antibody or fragment thereof.

(21) The kit according to (20), wherein the protein has the amino acid sequence as shown in SEQ ID NO: 2 or a mutant thereof.

(22) The kit according to (20) or (21), wherein the protein fragment comprises an epitope having at least 8 amino acids.

(23) The kit according to any of (20) to (22), wherein the urothelial cancer is selected from the group consisting of bladder cancer, renal pelvis cancer, urinary duct cancer, and urinary tract cancer.

(24) The kit according to any of (20) to (23), wherein the antibody or a fragment thereof is bound to a solid-phase support.

(25) The kit according to any of (20) to (24), which further comprises a labeled secondary antibody capable of binding to the antibody or a fragment thereof.

(26) The kit according to (25), wherein the label of the secondary antibody is an enzyme, fluorescent, or radioactive label.

(27) A kit for diagnosing a urothelial cancer comprising a nucleic acid consisting of the nucleotide sequence as shown in SEQ ID NO: 1 or a mutant thereof, a nucleic acid consisting of a sequence complementary thereto, a nucleic acid hybridizing under stringent conditions to the nucleic acid, a fragment comprising 15 or more continuous nucleotides thereof, or a chemically modified derivative of any thereof.

(28) The kit according to (27), wherein the nucleic acid has the nucleotide sequence as shown in SEQ ID NO: 1 or a mutant thereof.

(29) The kit according to (27) or (28), wherein the urothelial cancer is selected from the group consisting of bladder cancer, renal pelvis cancer, urinary duct cancer, and urinary tract cancer.

(30) The kit according to any of (27) to (29), wherein the nucleic acid is bound to a solid-phase support.

(31) The kit according to (30), wherein the solid-phase support is a DNA chip or microarray substrate.

(32) Use of the kit according to any of (20) to (31) in detecting a urothelial cancer of a subject in vitro.

DEFINITION

The terms used herein are defined as below.

Indications of nucleic acids, nucleotides, polynucleotides, amino acids, peptides, polypeptides, proteins, or the like by abbreviations are in accordance with "Guidelines for the preparation of specification which contain nucleotide and/or amino acid sequence" (Japan Patent Office) and common practice in the art.

The term "CXCL1" (chemokine (C-X-C motif) ligand 1, GRO-α, GRO-1, melanoma growth stimulating activity, alpha) protein used herein refers to a protein having a molecular weight of about 1.1 kDa consisting of 107 amino acid-residues belonging to the C-X-C chemokine family. This protein functions as a CXCR1 or CXCR2 ligand, which is a 7-transmembrane receptor, and induces migration of, for example, neutrophiles, basophiles, or mast cells that express such receptors (e.g., Richmond, A. et al., 1988, EMBO Journal, vol. 7, pp. 2025-712033). Also, the activity of CXCL1 as a mitogenetic factor in human malignant melanoma has been reported (Anisowicz, A. et al., 1987, Proceedings of the national Academy of Sciences, USA, vol. 84, pp. 7188-7192).

The term "nucleic acid" used herein refers to a nucleic acid including RNA or DNA. Such DNAs include cDNA, genomic DNA, and synthetic DNA. Such RNA includes total RNA, mRNA, rRNA, and synthetic RNA. The term "nucleic acid" used herein is interchangeably used with a polynucleotide.

The term "cDNA" as used herein refers to a full-length DNA strand of a sequence complementary to RNA resulting from gene expression, or a DNA fragment consisting of a partial sequence thereof cDNA can be synthesized via reverse transcriptase-polymerase chain reaction (RT-PCR) using RNA as a template and a poly T primer.

The term "gene" as used herein refers to not only double-stranded DNA but also single-stranded DNA such as a plus-strand (or a sense strand) or a complementary strand (or an antisense strand) constituting double-stranded DNA. It is not particularly limited by the length of such strand. Accordingly, the term "gene" refers to any of double-stranded DNA (including human genomic DNA), single-stranded DNA (plus-strand) (including cDNA), single-stranded DNA having a sequence complementary to the plus-strand (complementary strand), and a fragment thereof, unless otherwise specified. Such "gene" includes not only a "gene" represented by a specific nucleotide sequence (or a SEQ ID NO.) but also another "gene" encoding a protein, which has a biological function equivalent to that of a protein coded by said gene, such as a homolog, a mutant such as a splice variant, and a derivative. Specific examples of the "genes" encoding such homolog, variant, or derivative include "genes" each having a nucleotide sequence which hybridizes to a sequence complementary to a specific nucleotide sequence as shown in SEQ ID NO: 1 under stringent conditions as described below.

Examples of human-derived protein homologs or genes encoding the same include proteins or genes derived from other organism species corresponding to the human proteins or human genes encoding the same. Such protein homologs or gene homologs can be identified by HomoloGene. Specifically, a certain human amino acid or nucleotide sequence can be subjected to the BLAST programs (Karlin, S. et al., Proceedings of the National Academic Sciences, U.S.A., 1993, vol. 90, pp. 5873-5877) to obtain the accession number of the corresponding sequence (i.e., the sequence exhibiting the highest score, E-value 0, and identity 100%). Examples of the known BLAST programs include BLASTN (gene) and BLASTX (protein). When searching for a gene, for example, the accession number obtained from the above-mentioned BLAST search is inputted into the UniGene, and the obtained UniGeneClusterID (the number identified with "Hs.") is then inputted into the HomoloGene. From the list that shows the correlation of gene homologs between the genes of other organism species and the human genes, a gene of the other organism species can be selected as a gene homolog corresponding to the human gene represented by a given nucleotide sequence. In this procedure, the FASTA program may be used instead of the BLAST program.

Functional regions of "genes" are not limited, and examples thereof include expression-control regions, coding regions, and exon or intron regions.

The term "transcription product" as used herein refers to messenger RNA (mRNA) which is synthesized from the DNA sequence of a gene as a template. Messenger RNA is synthesized by binding of RNA polymerase to a site called promoter, which is located upstream of the gene of interest, and subsequently by binding of ribonucleotides to the 3' end so as to be complementary to the nucleotide sequence of DNA. Such messenger RNA contains not only the gene of interest but also a full-length sequence spanning from a transcription initiation site to the terminus of a poly A sequence including expression control region, coding region, and exon or intron region.

The term "translation product" as used herein refers to a protein which is synthesized based on the information of messenger RNA synthesized via transcription regardless of modification such as splicing. During the translation process of messenger RNA, ribosome first binds to messenger RNA, and amino acids are then linked in accordance with the nucleotide sequence of messenger RNA, thereby leading to the synthesis of a protein.

The term "probe" as used herein refers to a nucleic acid which is used for specifically detecting RNA resulting from gene expression or a nucleic acid derived therefrom and/or a nucleic acid complementary thereto.

The term "primer" as used herein refers to a continuous nucleic acid that specifically recognizes and amplifies RNA resulting from gene expression or a nucleic acid derived therefrom, and/or a nucleic acid complementary thereto.

The complementary nucleic acid (i.e., a complementary strand or reverse strand) refers to a nucleic acid that is basically complementary to the full-length sequence of a nucleic acid having a nucleotide sequence as shown in a given SEQ ID NO. or a partial sequence thereof (herein, conveniently referred to as a "plus strand"), on the basis of the base pairing like A:T(U) or G:C. Such a complementary strand, however, is not limited to a sequence completely complementary to the nucleotide sequence of a plus strand of interest; that is, the complementary strand may have such a complementarity that it can hybridize to the plus strand under stringent conditions.

As used herein, the "stringent conditions" means such conditions that a probe can hybridize to a target sequence with a higher degree of detection when compared with its hybridization to other sequences (e.g., at least twice the background). Stringent conditions are dependent on the sequence of a target, varying depending on the environment where hybridization takes place. By controlling stringency of hybridization and/or washing conditions, a target sequence that is 100% complementary to the probe can be identified.

As used herein, the term "mutant (or variant)" in case of a nucleic acid refers to a naturally-occurring mutant resulting from polymorphism, mutation, alternative splicing during transcription, or the like, a homolog thereof, a mutant based on degeneracy of genetic cord, a mutant comprising a deletion, substitution, addition, or insertion of one or more nucleotides, preferably one or several nucleotides, in a nucleotide sequence as shown in SEQ ID NO: 1 or a partial sequence thereof, a mutant having at least about 80%, at least about 85%, at least about 90%, at least about 95%, at least about 97%, at least about 98%, or at least about 99% identity with said nucleotide sequence or said partial sequence thereof, or a nucleic acid mutant that hybridizes to a polynucleotide or oligonucleotide comprising said nucleotide sequence or partial sequence thereof under the stringent conditions as defined above. On the other hand, a "mutant (or variant)" in case of a protein or peptide refers to a mutant comprising a deletion, substitution, addition, or insertion of one or more amino acids, preferably one or several amino acids, in an amino acid sequence as shown in any of SEQ ID NO: 2 or a partial sequence thereof, or a mutant having a % identity of at least about 80%, at least about 85%, at least about 90%, at least about 95%, at least about 97%, at least about 98%, or at least about 99% with said amino acid sequence or partial sequence thereof.

The term "several" as used herein means an integer of about 10, 9, 8, 7, 6, 5, 4, 3, or 2.

As used herein, the "% identity" can be determined by using a protein or gene searching system such as BLAST or FASTA as mentioned above, with introducing a gap (Karlin, S. et al., 1993, Proceedings of the National Academic Sciences, U.S.A., vol. 90, pp. 5873-5877; Altschul, S. F. et al., 1990, Journal of Molecular Biology, vol. 215, pp. 403-410; Pearson, W. R. et al., 1988, Proceedings of the National Academic Sciences, U.S.A., vol. 85, pp. 2444-2448).

As used herein, the term "derivative" in case of a nucleic acid refers to a derivative labeled with fluorophore, radioisotope, or the like, a derivative comprising a modified nucleotide (e.g., a nucleotide having a functional group such as halogen, alkyl (e.g., methyl), alkoxy (e.g., methoxy), thio, or carboxymethyl; a biotinylated nucleotide; or a nucleotide comprising, for example, reconstitution of a base, saturation of a double bond, deamination, or substitution of oxygen by sulfur), or the like. On the other hand, a "derivative" in case of a protein refers to a chemically modified derivative, such as an acetylated, acylated, alkylated, phosphorylated, sulfated, glycosylated, or biotinylated/avidinylated derivative or a derivative labeled with an enzyme, fluorophore, luminophore, or the like.

As used herein, the term "a kit for diagnosis (or detection or determination)" refers to a kit that is directly or indirectly employed for diagnosing the presence or absence of the development of a urothelial cancer, the degree of advancement, the presence or absence of the amelioration, or the degree of the amelioration (i.e., whether this disease is ameliorated or is not ameliorated), or for screening for candidate substances useful for preventing, ameliorating, or treating the urothelial cancer. The kit comprises a nucleotide, an oligonucleotide, or a polynucleotide, which can specifically recognize and bind to a gene whose expression varies or fluctuates in vivo, in particularly urothelial tissue, associated with the development of the urothelial cancer. Such oligonucleotide and polynucleotide can be effectively used as a probe for detecting the aforementioned gene that is expressed in vivo, in tissue, or in a cell, based on the aforementioned properties, or as a primer for amplifying the gene expressed in vivo. The kit also comprises an antibody that can detect a protein as a translation product of the aforementioned gene.

As used herein, the "biological sample" to be detected or diagnosed refers to a sample (or a specimen) in which the expression pattern of the protein and/or gene of the invention changes with the development of urothelial cancer and which is taken from a subject. More specifically, the sample means an urothelial tissue and its peripheral lymph nodes, another organ suspected of metastasis, body fluid such as blood, blood serum, blood plasma, a culture supernatant of lymphocytes, urine, spinal fluid, saliva, sweat, or ascites, and cell or organ extracts.

The term "urothelial cancer" as used herein refers to a cancer that is developed on the transitional epitheliums of calices, renal pelvis, urinary duct, bladder, and urinary tract. Examples of urothelial cancer include bladder cancer, renal pelvis cancer, urinary duct cancer, and urinary tract cancer. The present invention is particularly preferably used for detecting bladder cancer.

The term "subject" as used herein refers to an animal having urothelial cancer, preferably a mammalian animal having urothelial cancer, and more preferably a human having urothelial cancer.

The term "specific (or specifically)" as used herein refers to selectively recognizing a given protein or nucleic acid alone, or selectively binding thereto or reacting therewith.

ADVANTAGES OF THE INVENTION

The present invention enables easy and highly reliable detection of a urothelial cancer. For example, assay of the ratio of CXCL1 level to creatinine level in the patient's urine enables the easy diagnosis of urothelial cancer. The present invention is particularly effective for detecting infiltrative tumors.

This description includes all or part of the contents as disclosed in the description and/or drawings of Japanese Patent Application No. 2005-255370, which is a priority document of the present application.

PREFERRED EMBODIMENTS OF THE INVENTION

Figure 1:
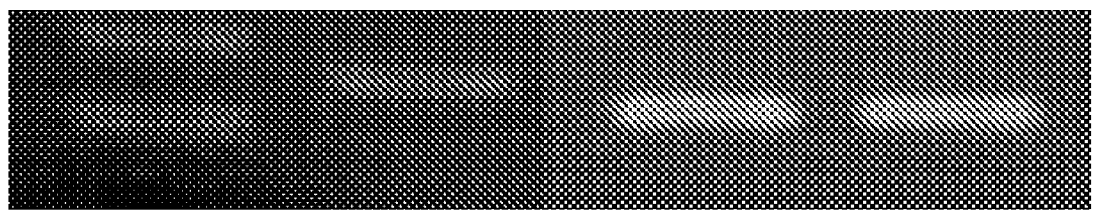
FIG. 1 shows the results of a comparison of CXCL1 mRNA expression levels measured via RT-PCR in the established bladder cancer cells and in the normal urothelial cells.

We had conducted screening via proteome analysis of cell culture supernatants for proteins whose expression levels are enhanced in cancer cells obtained from bladder cancer patients compared with normal urothelial cells. As a result, we have now found that a greater amount of full-length CXCL1 protein was detected in culture supernatants of cancer cells than in culture supernatants of normal urothelial cells. The term "normal urothelial cells" used herein refers to epidermic cells obtained from normal urinary ducts of patients that were subjected to nephrectomy but were not afflicted with urothelial cancer.

Also, we measured the CXCL1 protein level in the blood and the urine before and after extirpation of cancer from a bladder cancer patient by an immunological method. As a result, we have now found that the amount of the CXCL1 protein in the blood and the urine of the patient before bladder cancer extirpation was higher than that after the extirpation of bladder cancer.

Further, we recovered total RNA expressed in cells obtained from a bladder cancer patient and in normal urothelial cells, and the expression level of the gene encoding CXCL1 in the total RNA was measured by the DNA array method and quantitative PCR method. Thus, the amount of mRNA that codes CXCL1 was found to be increased in comparison with the normal cells in cells obtained from the bladder cancer patient.

Accordingly, in one aspect of the present invention, there is provided a method for detecting a urothelial cancer comprising determining the CXCL1 protein, or the expression of a gene encoding the protein, in vitro in biological samples from patients.

According to the method of the present invention, in general, the presence or existing amount of the protein or the expression or expression level of the gene is measured in a biological sample. The target protein or gene in the present invention includes a mutant resulting from polymorphism in accordance with a type of a subject (e.g., a race) or an individual or splicing mutation. The presence or amount of the protein or the expression or expression level of the gene can be measured using a substance that can bind specifically to such protein or gene. Examples of such substance include an antibody and a nucleic acid probe as described below.

An antibody that can be used in the present invention is an antibody that recognizes and binds specifically to the CXCL1 protein (preferably a protein having the amino acid sequence as shown in SEQ ID NO: 2), a fragment thereof, or a chemically modified derivative thereof (as defined above). Examples of antibodies include a polyclonal antibody, a monoclonal antibody, and antibody fragments, such as Fab, Fab', F(ab')$_2$, Fv, and scFv. The antibody of the present invention reacts with one or a plurality of epitopes comprising at least 5 and preferably at least 8 amino acids of the aforementioned protein. A specific polyclonal antibody can be prepared by a method whereby passing an antiserum of a rabbit or the like immunized with the CXCL1 protein, through a column filled with a support, such as agarose, to which the CXCL1 protein has been bound, and recovering the IgG antibody bound to the column support. A monoclonal antibody can be obtained by a method as described below.

The nucleic acid probes that can be used in the present invention include a nucleic acid consisting of the nucleotide sequence as shown in SEQ ID NO: 1 or a mutant thereof, a nucleic acid consisting of a sequence complementary thereto, a nucleic acid hybridizing under stringent conditions to such nucleic acid, a fragment comprising 15 or more continuous nucleotides thereof, or a chemically modified derivative thereof (as defined above).

According to the method of the present invention, the existing amount of the protein or the expression level of the gene in a biological sample is assayed in accordance with the embodiment. When the amount of the protein or the expression level of the gene is significantly increased over that of a control sample, a subjected is determined to be afflicted with urothelial cancer. A control sample is an equivalent sample obtained from a normal or healthy individual or an individual having no urothelial cancer. Examples of such sample include body fluid such as blood or urine and urothelial tissue or cells. In particular, mRNA is recovered from tissue or cell samples in accordance with a conventional technique, and the amount of cDNA generated and amplified via quantitative RT-PCR (wherein this amount corresponds to the expression level of the target gene) is determined. Alternatively, the cells are cultured and the level or concentration of the CXCL1 protein in the culture supernatant can be determined.

The amount of increase relative to the control sample is generally twice or more, preferably three times or more, more preferably 4 times or more, and most preferably 5 times or more. If such increase is 3 times or more, reliability is enhanced. The degree of increase can be determined not only by comparison of the measured values. For example, using the amount of a certain correction substance (e.g., creatinine) as a reference, the degree of increase can also be determined by comparing relative values of the measured values to the amount of the correction substance.

As defined above, examples of the urothelial cancers include bladder cancer, renal pelvis cancer, urinary duct cancer, and urinary tract cancer. In the case of detection of bladder cancer, in particular, detection reliability of infiltrative tumor was significantly higher than that of superficial tumor. Accordingly, the present invention is particularly effective for detecting infiltrative tumor that is likely to cause metastasis among urothelial cancers.

Thus, the method for detecting a urothelial cancer according to the present invention comprises measuring the expression level of a nucleic acid derived from a gene encoding the CXCL1 protein produced from the urothelial cancer cell in a sample with the use of a primer or probe and immunologically measuring the CXCL1 protein, in the sample, produced by the urothelial cancer cell using an antibody. According to the method of the present invention, whether or not the subject suffers from urothelial cancer can be determined, and a patient with urothelial cancer can also be distinguished from a patient without urothelial cancer. Furthermore, quantification of the expression level of a nucleic acid derived from a gene encoding the CXCL1 protein or the CXCL1 protein level in a sample by the method of the present invention enables determination of the progress of a urothelial cancer.

In one embodiment, the present invention provides a method for detecting a urothelial cancer, which is represented by bladder cancer, by immunologically quantifying the CXCL1 protein in a sample using an antibody or fragment thereof that binds specifically to the CXCL1 protein or a fragment thereof.

Alternatively, in another embodiment, the present invention provides a method for detecting a urothelial cancer, which is represented by bladder cancer, by measuring the expression level of a gene encoding the CXCL1 protein in a sample using a nucleic acid consisting of a nucleotide sequence encoding the CXCL1 protein, a nucleic acid consisting of a sequence complementary thereto, a nucleic acid hybridizing under stringent conditions to such nucleic acid, or a fragment comprising 15 or more continuous nucleotides thereof.

Detection of CXCL1 Gene:

In the present invention, one example of a method for detecting urothelial cancer is a method wherein the expression level of a gene encoding the CXCL1 protein produced from the urothelial cancer cell in a sample is measured with the use of a nucleic acid as a primer or probe.

In the present invention, the nucleic acid that can be used for determining the presence and/or absence of a urothelial cancer or for diagnosing urothelial cancer enables a qualitative and/or quantitative measurement of the presence, expression level, or existing amount of the human-derived CXCL1 gene, a homolog thereof, a transcription product or cDNA thereof, or a mutant or derivative thereof.

The expression level of the CXCL1 gene is significantly increased in a urothelial cancer tissue compared with the corresponding non-cancerous tissue. Accordingly, the composition of the present invention can be effectively used for assaying and comparing the expression levels of the CXCL1 gene in noncancerous tissue and in urothelial cancer tissue.

Examples of nucleic acids that can be used in the present invention include 1 or a combination of a plurality of nucleic acids selected from the group consisting of a nucleic acid comprising the nucleotide sequence as shown in SEQ ID NO: 1 and a sequence complementary thereto, a nucleic acid hybridizing under stringent conditions to DNA comprising a nucleotide sequence complementary to the nucleotide sequence and a sequence complementary thereto, a nucleic acid comprising 15 or more continuous nucleotides of the nucleic acid sequences.

Fragments of the polynucleotide above can include, but are not limited to, nucleotide sequences of, for example, continuous 15 to all nucleotides, 15 to 300 nucleotides, 15 to 250 nucleotides, 15 to 200 nucleotides, 15 to 150 nucleotides, 15 to 140 nucleotides, 15 to 130 nucleotides, 15 to 120 nucleotides, 15 to 110 nucleotides, 15 to 100 nucleotides, 15 to 90 nucleotides, 15 to 80 nucleotides, 15 to 70 nucleotides, 15 to 60 nucleotides, 15 to 50 nucleotides, 15 to 40 nucleotides, 15 to 30 nucleotides or 15 to 25 nucleotides; 25 to all nucleotides, 25 to 300 nucleotides, 25 to 250 nucleotides, 25 to 200 nucleotides, 25 to 150 nucleotides, 25 to 140 nucleotides, 25 to 130 nucleotides, 25 to 120 nucleotides, 25 to 110 nucleotides, 25 to 100 nucleotides, 25 to 90 nucleotides, 25 to 80 nucleotides, 25 to 70 nucleotides, 25 to 60 nucleotides, 25 to 50 nucleotides or 25 to 40 nucleotides; 50 to all nucleotides, 50 to 300 nucleotides, 50 to 250 nucleotides, 50 to 200 nucleotides, 50 to 150 nucleotides, 50 to 140 nucleotides, 50 to 130 nucleotides, 50 to 120 nucleotides, 50 to 110 nucleotides, 50 to 100 nucleotides, 50 to 90 nucleotides, 50 to 80 nucleotides, 50 to 70 nucleotides or 50 to 60 nucleotides; 60 to all nucleotides, 60 to 300 nucleotides, 60 to 250 nucleotides, 60 to 200 nucleotides, 60 to 150 nucleotides, 60 to 140 nucleotides, 60 to 130 nucleotides, 60 to 120 nucleotides, 60 to 110 nucleotides, 60 to 100 nucleotides, 60 to 90 nucleotides, 60 to 80 nucleotides or 60 to 70 nucleotides; and the like.

The nucleic acids or fragments thereof as used in the invention may be either DNA or RNA.

Nucleic acids in the composition of the present invention can be prepared by common techniques such as recombinant DNA technology, PCR, or a method of using an automatic DNA/RNA synthesizer.

Recombinant DNA technology or PCR can include the use of the techniques as disclosed in, for example, Ausubel. et al., Current Protocols in Molecular Biology, John Willey & Sons, US (1993); or Sambrook et al., Molecular Cloning: A Laboratory Manual, Cold Spring Harbor Laboratory Press, US (1989).

The present invention also provides a kit for diagnosing (or detecting) a urothelial cancer comprising one or more of a nucleic acid, which can be used as a probe (occasionally as a primer) in the aforementioned method, a mutant thereof, and/or a fragment thereof.

The kit of the present invention preferably comprises 1 or a plurality of nucleic acids selected from the nucleic acids mentioned above or a fragment thereof.

The kit of the present invention can comprise at least one of a nucleic acid consisting of the nucleotide sequence as shown in SEQ ID NO: 1, a nucleic acid consisting of a sequence complementary thereto, a nucleic acid hybridizing under stringent conditions to such nucleic acid, and a fragment of such nucleic acid.

According to a preferable embodiment, the nucleic acid is a nucleic acid comprising the nucleotide sequence as shown in SEQ ID NO: 1, a nucleic acid comprising a sequence complementary thereto, a nucleic acid hybridizing under stringent conditions to such nucleic acid, or a fragment comprising 15 or more continuous nucleotides thereof.

According to a preferable embodiment, the fragment can be a nucleic acid comprising continuous, nucleotides such as 15 or more, preferably 30 or more, more preferably 50 or more, or far more preferably 60 or more nucleotides, for example 50 to 100 nucleotides.

The above combinations that constitute the kit of the present invention are merely illustrative, and any other types of possible combinations fall within the scope of the present invention.

The nucleic acids, mutants thereof, and fragments thereof, which can be contained in the kit of the present invention, may be packaged in different containers separately or in any combination.

The nucleic acid as a probe to be contained in the kit of the present invention may be bound to a solid-phase support. Examples of the support include substrates such as DNA microarray or DNA chip. Specifically, the DNA microarray or DNA chip comprising the above nucleic acid also falls within the scope of the present invention.

Nucleic acids to be immobilized include all the nucleic acids of the present invention as mentioned above. For example, such nucleic acid can comprise 1 or a plurality of nucleic acids or fragments thereof as shown below:

a nucleic acid consisting of the nucleotide sequence as shown in SEQ ID NO: 1, a mutant thereof, or a fragment thereof comprising 15 or more continuous nucleotides;

a nucleic acid comprising the nucleotide sequence as shown in SEQ ID NO: 1;

nucleic acids each hybridizing under stringent conditions to DNA consisting of a nucleotide sequence complementary to the nucleotide sequence as shown in SEQ ID NO: 1 or a fragment thereof comprising 15 or more continuous nucleotides;

nucleic acids each hybridizing under stringent conditions to DNA consisting of the nucleotide sequence as shown in SEQ ID NO: 1 or a fragment thereof comprising 15 or more continuous nucleotides; and a nucleic acid comprising 60 or more continuous nucleotides of the nucleotide sequence as shown in SEQ ID NO: 1 or a sequence complementary thereto.

According to the present invention, the nucleic acids to be immobilized may be any of genomic DNA, cDNA, RNA, synthetic DNA, and synthetic RNA, or alternatively they may be single-stranded or double-stranded.

Examples of DNA chips that can detect and measure the expression levels of the target gene, RNA, or cDNA include the Gene Chip Human Genome U133 Plus 2.0 Array (Affymetrix), the Whole human genome oligo microarray (Agilent), the IntelliGene® HS Human Expression CHIP (Takara Bio).

DNA microarrays can be prepared by, for example, a method wherein probes that have been prepared in advance are immobilized on a solid-phase surface. In this method, polynucleotides into which functional groups have been introduced are synthesized, and oligonucleotides or polynucleotides are spot-deposited on the surface of a surface-treated solid-phase support, followed by covalently binding to the surface (e.g., J. B. Lamture et al., Nucleic. Acids. Research, 1994, vol. 22, pp. 2121-2125; Z. Guo et al., Nucleic. Acids. Research, 1994, vol. 22, pp. 5456-5465). In general, the nucleic acids are covalently bound to the surface-treated solid-phase support via a spacer or crosslinker. The method wherein fine pieces of polyacrylamide gel are aligned on the glass surface and synthetic nucleic acids are covalently bound thereto is also known (G. Yershov et al., Proceedings of the National Academic Sciences, U.S.A., 1996, vol. 94, p. 4913). As a further method, a microelectrode array is prepared on silica microarray, on which electrode is formed a reaction site by making a permeable layer of streptavidin-containing agarose, where this site is positively charged to immobilize the biotinylated polynucleotides thereon and the charge at the site is regulated, then this makes the stringent hybridization at a high speed possible (R. G Sosnowski et al., Proceedings of the National Academic Sciences, U.S.A., 1997, vol. 94, pp. 1119-1123).

A substrate of the DNA chip is not particularly limited, provided that the substrate can comprise DNAs immobilized thereon. Examples of the substrate include a glass slide, a silicon chip, a polymer chip, and a nylon membrane. Such substrates may be subjected to surface treatment, for example, poly-L-lysine coating or introduction of a functional group like amino group or carboxyl group.

DNA can be immobilized on a substrate by any common techniques without particular limitation. Examples of such techniques include a method wherein DNA is spotted using a high-density dispenser, called spotter or arrayer, a method of spraying DNA on a substrate using an apparatus (i.e., inkjet), which jets fine droplets from a nozzle by a piezoelectric element, and a method of synthesizing nucleotides successively on a substrate. When the high-density dispenser is used, for example, different gene solutions are first placed into each well of a multi-well plate, and the solutions are taken out of the plate using a pin (i.e., needle) and are successively spotted on the substrate. According to the inkjet technique, genes are jetted through a nozzle, and the genes are arrayed on the substrate at a high speed. In the DNA synthesis on the substrate, a nucleotide on the substrate is protected with a functional group, which is capable of leaving from the substrate by light, and light is selectively applied only to a nucleotide at a specific position by using a mask, thereby deprotecting the functional group. Thereafter, nucleotides are added to the reaction mixture, which nucleotides are coupled to the nucleotides on the substrate, and this step is repeated.

Hybridization conditions are not particularly limited. For example, hybridization is carried out in 3 to 4×SSC and 0.1% to 0.5% SDS at 30° C. to 50° C. for 1 to 24 hours, more preferably in 3.4×SSC and 0.3% SDS at 40° C. to 45° C. for 1 to 24 hours, followed by washing. Washing is continuously carried out, for example, with a solution containing 2×SSC and 0.1% SDS, with a solution of 1×SSC, and with a solution of 0.2×SSC at room temperature. The term "1×SSC" refers to an aqueous solution containing 150 mM sodium chloride and 15 mM sodium citrate (pH 7.2). Preferably, a complementary strand remains hybridized to the target (+) strand even if it is washed under such conditions. Specific examples of such complementary strand include a strand consisting of the nucleotide sequence completely complementary to the nucleotide sequence of the target (+) strand, and a strand consisting of a nucleotide sequence having at least 80% identity with said strand.

When PCR is carried out under stringent hybridization conditions using polynucleotide fragments obtained from the kit of the present invention as primers, for example, a PCR buffer comprising 10 mM Tris-HCl (pH 8.3), 50 mM KCl, and 1 to 2 mM $MgCl_2$ is used, and the treatment is carried out at a melting temperature, Tm—(5 to 10° C.), which is calculated from the primer sequence, for about 15 seconds to 1 minute. The Tm value can be calculated, for example, by the equation $T_m = 2\times$(the number of adenine residues+the number of thymine residues)+4×(the number of guanine residues+the number of cytosine residues).

Another example of the "stringent conditions" for hybridization is described in, for example, Sambrook, J. & Russel, D., Molecular Cloning, A LABORATORY MANUAL, Cold Spring Harbor Laboratory Press, Jan. 15, 2001, vol. 1: 7.42 to 7.45, vol. 2: 8.9 to 8.17, and such conditions can be employed in the present invention.

Detection of CXCL1 Protein:

In the present invention, another example of the method for detecting a urothelial cancer is a method wherein the expression or amount of the CXCL1 protein produced in the urothelial cancer cell in the sample is measured using an antibody.

In the present invention, the antibodies that can be used for determining the presence and/or absence of urothelial cancer or for diagnosing urothelial cancer enables qualitative and/or quantitative assay of the expression level or amount of the translation product of the human-derived CXCL1 gene, a homolog thereof, a mutant thereof, or a derivative thereof.

The antibodies that can be used in the present invention are not particularly limited, provided that they can bind specifically to the CXCL1 protein or fragments thereof. The antibody usable in the invention is a monoclonal or polyclonal antibody, preferably monoclonal antibody. The globulin type of the antibody of the present invention is not particularly limited, as long as the antibody has the aforementioned properties, and may be any of IgG, IgM, IgA, IgE, and IgD, preferably IgG and IgM. For example, the monoclonal antibody 21326.1 (ab10375, Abcam) can be used, and the polyclonal antibody commercially available from Abcam can be used. Alternatively, an antibody that binds specifically to the CXCL1 protein can be prepared in accordance with a method described below.

Preparation of Immunogen:

In order to prepare an antibody in the present invention, protein as an immunogen (antigen) is prepared, As an immunogen protein, the CXCL1 protein or a fragment thereof is used. The amino acid sequence (SEQ ID NO: 2) of the CXCL1 protein that can be used as an immunogen in the present invention, and the cDNA sequence (SEQ ID NO: 1) encoding the protein, are disclosed under the accession numbers NP_001502 and NM_001511 in the GenBank. Accordingly, a fragment of the CXCL1 protein to be used as an immunogen can be synthesized with the utilization of the disclosed amino acid sequence information in accordance with a method known in the art, such as a solid-phase peptide synthesis method. When a fragment of the CXCL1 protein is used as an immunogen, it is preferably ligated to a carrier protein, such as KLH or BSA.

The CXCL1 protein can be obtained with the use of information of cDNA encoding the CXCL1 protein by known recombinant DNA techniques. cDNA encoding the CXCL1 protein can be prepared by cDNA cloning. Total RNA is extracted from a tissue of a living body, such as monocyte, melanoma cell, respiratory epithelial cell, keratinocyte, or alveolar macrophage, in which the target CXCL1 gene of the present invention is expressed, the extracted total RNA is applied to the oligo dT cellulose column to obtain poly A(+) RNA, cDNA library is prepared therefrom by RT-PCR, and the target cDNA clones can be obtained from the resulting library by a screening method such as hybridization screening, expression screening, or antibody screening. If necessary, the cDNA clones may be amplified by PCR. Probes or primers can be selected and synthesized from any sequences comprising 15 to 100 continuous nucleotides in the nucleotide sequences as shown in SEQ ID NO: 1. The cDNA cloning technique is described in, for example, Sambrook, J. & Russel, D., Molecular Cloning, A LABORATORY MANUAL, Cold Spring Harbor Laboratory Press, Jan. 15, 2001, vol. 1: 7.42 to 7.45, vol. 2: 8.9 to 8.17.

The CXCL1 protein can be obtained by, for example, incorporating a cDNA clone obtained in the above manner into an expression vector, culturing prokaryotic or eukaryotic host cells transformed or transfected with the vector, and obtaining the CXCL1 protein from the cells or culture supernatant. Examples of the expression vector include *E. coli*-derived plasmids (for example, pET21a, pGEX4T, pC118, pC119, pC18, or pC19), *Bacillus subtilis*-derived plasmids (for example, pUB110 and pTP5), and yeast-derived plasmids (for example, YEp13, YEp24, or YCp50). An example of phage DNA is λphage (for example, λgt11 or λZAP). Further, animal virus vectors such as vaccinia virus vector or insect virus vectors such as baculovirus vector can also be used. The vectors and the expression systems are available from Novagen, Takara Shuzo (Japan), Daiichi Pure Chemicals (Japan), Qiagen, Stratagene, Promega, Roche Diagnostics, Invitrogen, Genetics Institute, or Amersham Bioscience.

cDNA of CXCL1 is inserted into a vector by first cleaving the purified DNA with an adequate restriction enzyme, and inserting the resultant into a restriction enzyme site or multi-cloning site of an adequate vector to ligate cDNA to the vector. Vectors can comprise, in addition to DNA encoding the aforementioned protein, regulatory elements such as promoter, enhancer, polyadenylation signal, ribosome-binding site, replication origin, terminator, and selection marker. Moreover, in order, to facilitate the purification of a polypeptide, a peptidic label may be added to the C- or N-terminus of the polypeptide to form a fusion polypeptide. Examples of representative peptidic labels include, but are not limited to, (histidine)$_{6-10}$ repeat, FLAG, myc peptide, and GFP protein. The recombinant DNA techniques are described in Sambrook, J. & Russel, D. (supra). A DNA fragment is ligated to a vector fragment using a known DNA ligase.

Examples of host cells that can be used are procaryotic cells such as bacteria (e.g., *E. coli* or *Bacillus subtilis*), yeast (e.g., *Saccharomyces cerevisiae*), insect cells (e.g., Sf cells), and mammalian cells (e.g., COS, CHO, and BHK cells). A method for introducing a recombinant vector into a host cell is not particularly limited, provided that such method is for introducing DNA into a relevant host cell. For example, a method involving the use of calcium ions, a method involving the use of liposome, electroporation, or microinjection can be employed.

As a medium for culturing a transformant obtained with the use of a microorganism such as *E. coli* or yeast as a host, either a natural or synthetic medium may be used as long as it contains carbon sources, nitrogen sources, and inorganic salts assimilable by the microorganism and is capable of efficiently culturing the transformant. Culture is generally conducted under aerobic conditions, for example, via shake culture or aeration agitation culture, at 37° C. for 6 to 24 hours. During the culture, a pH level is maintained at around neutral. A pH level is adjusted using inorganic or organic acid, an alkaline solution, or the like. During the culture, an antibiotic such as ampicillin or tetracycline may be added to the medium, if necessary. When culturing transformants of mammalian cells, such cells are cultured in a suitable medium, and proteins generated in the culture supernatant or cells are recovered. In such a case, a medium may or may not comprise blood serum, with culture in a serum-free medium being preferable. When the CXCL1 protein is produced in the microorganisms or cells, such microorganisms or cells may be disrupted to extract proteins. When the CXCL1 protein is secreted outside the microorganisms or cells, the culture broth may be used in that state or subjected to centrifugation or another procedure to remove the microorganisms or cells.

When the proteins of the present invention are produced without the addition of a peptidic label, the protein can be purified by, for example, ultrafiltration, salting out, gel filtration, or ion-exchange chromatography. In addition to this, affinity chromatography, HPLC, hydrophobic chromatography, isoelectric chromatography, or the like may be carried out in combination. When the protein has a peptidic label, such as histidine repeat, FLAG, myc, or GFP, an affinity chromatography suitable for each peptidic label can be carried out in accordance with conventional techniques. Construction of an expression vector that facilitates isolation or purification is preferable. When the expression vector is constructed so as to express in the form of the fusion protein of a polypeptide with a peptidic label and such vector is used to prepare the protein by genetic engineering techniques, the isolation or purification of the polypeptide is easy. Whether or not the CXCL1 protein was obtained could be confirmed by SDS-polyacrylamide gel electrophoresis or other means.

The thus-obtained antibody that recognizes the protein can bind specifically to the protein via an antigen-binding site of the antibody. Specifically, the CXCL1 protein, a fragment thereof, a mutant thereof, a fusion protein, or the like can be used as an immunogen to produce immunoreactive antibodies.

More specifically, the protein, a fragment thereof, a mutant thereof, or a fusion protein comprises an antigenic determinant or epitope that elicits antibody formation, which antigen determinant or epitope may have a linear structure or a higher-order (or disconnected) structure. Such antigen determinant or epitope can be identified by any method known in the art.

Antibodies of any aspect are elicited by the proteins of the present invention. If all, part, or an epitope of the protein is isolated, a polyclonal or monoclonal antibody can be prepared in accordance with conventional techniques. An example of the method for preparing an antibody is described in Kennet et al. (ed.), Monoclonal Antibodies, Hybridomas: A New Dimension in Biological Analyses, Plenum Press, New York, 1980.

Subsequently, the resulting protein is dissolved in a buffer to prepare an immunogen. If necessary, an adjuvant may be added in order to facilitate immunization. Examples of an adjuvant include a commercially available Freund's complete adjuvant, Freund's incomplete adjuvant, aluminum hydroxide (alum), and muramyl peptide. Any of such adjuvant may be used in admixture.

Preparation of Monoclonal Antibody:

(1) Immunization and Collection of Antibody-Producing Cell

The immunogen thus obtained is administered to a mammalian animal such as rat, mouse (e.g., the inbred mouse strain Balb/c), or rabbit. The dose of the immunogen is appropriately determined depending on, for example, the type of an animal to be immunized or the route of administration, and it is about 50 to 200 µg per animal. Immunization is primarily performed by injecting an immunogen subcutaneously or intraperitoneally. The intervals of immunization are not particularly limited. After the primary immunization, boost immunization is carried out 2 to 10 times, preferably 3 or 4 times, at the intervals of several days to several weeks, and preferably at the intervals of 1 to 4 weeks. After the primary immunization, the antibody titer of the blood serum of the immunized animal is repeatedly measured by, for example, enzyme-linked immuno sorbent assay (ELISA). When the antibody titer reached a plateau, the immunogen is injected intravenously or intraperitoneally to complete the final immunization. The antibody-producing cells are recovered 2 to 5 days, preferably 3 days, after the final immunization. Examples of antibody-producing cells include spleen cells, lymph node cells, and peripheral blood cells, preferably spleen cells or regional lymph node cells.

(2) Cell Fusion

The present invention also provides hybridoma cell lines that produce monoclonal antibodies specific for relevant proteins. Such hybridomas can be produced and identified via conventional techniques. The method for producing such hybridoma cell lines comprises immunizing an animal with a protein of the invention, removing spleen cells from the immunized animal, fusing the spleen cells with a myeloma cell line, producing hybridoma cells therefrom, and determining a hybridoma cell line that produces a monoclonal antibody binding to the enzyme of interest. Myeloma cell lines to be fused with antibody-producing cells can be commercially available established cell lines of animals such as mice. Preferably, cell lines to be used have drug selectivity; namely, they cannot survive in the HAT selection medium (containing hypoxanthine, aminopterin, and thymine) in an unfused state, while they can survive only in a state fused with antibody-producing cells. The established cells are preferably derived from an animal of the same species with the animal to be immunized. An example of the myeloma cell line is the strain P3×63-Ag.8 (ATCC TIB9), which is a BALB/c mouse-derived hypoxanthine guanine phosphoribosyl-transferase (HGPRT) deficient cell line.

Subsequently, the myeloma cell lines are fused with the antibody-producing cells. Cell fusion is carried out in a serum-free medium for animal cell culture, such as DMEM or RPMI-1640 medium, by mixing the antibody-producing cells with the myeloma cell lines at about 1:1 to 20:1 in the presence of a cell fusion accelerator. As the cell fusion accelerator, polyethylene glycol having an average molecular weight of 1,500 to 4,000 daltons can be used at a concentration of about 10 to 80%, for example. Optionally, an auxiliary agent, such as dimethyl sulfoxide, can be used in combination in order to enhance the fusion efficiency. Further, the antibody-producing cells can be fused with the myeloma cell lines by using a commercially available cell fusion apparatus utilizing electric stimulus (e.g., electroporation).

(3) Selection and Cloning of Hybridomas

The hybridomas of interest are selected from the fused cells. To this end, the cell suspension is adequately diluted in, for example, a fetal bovine serum-containing RPMI-1640 medium, then the suspension is aliquoted into each well of a microtiter plate at about two million cells/well, to which wells are added a selection medium, and thereafter culture is carried out while appropriately exchanging the selection medium with the same fresh medium. The culture temperature is 20° C. to 40° C., preferably about 37° C. When the myeloma cell is an HGPRT-deficient strain or thymidine kinase-deficient strain, a hybridoma of a cell having an ability to produce an antibody and a myeloma cell line can selectively be cultured and grown in the selection medium containing hypoxanthine, aminopterin, and thymidine (i.e., the HAT medium). As a result, cells grown about 14 days after the initiation of culture in the selection medium can be obtained as the hybridoma.

Subsequently, whether or not the culture supernatant of the grown hybridoma contains the antibody of interest is screened for. Screening of hybridomas can be carried out in accordance with conventional techniques, without particular limitation. For example, the culture supernatant in the well containing the grown hybridomas is partially sampled and then subjected to enzyme immunoassay (EIA) or ELISA or radio immunoassay (RIA). The fused cells are cloned using the limiting dilution method or the like, and monoclonal antibody-producing cells, i.e. hybridomas, are established in the end. The hybridoma of the present invention is stable during the culture in a basic medium, such as RPMI-1640 or DMEM, as described below, and the hybridoma can produce and secrete a monoclonal antibody that reacts specifically with the CXCL1 protein derived from urothelial cancer.

(4) Recovery of Antibody

Monoclonal antibody can be recovered by conventional techniques. Specifically, a monoclonal antibody can be collected from the established hybridoma by the conventional cell culture technique, the ascites development, or the like. According to the cell culture technique, hybridoma is cultured in an animal cell culture medium, such as 10% fetal bovine serum-containing RPMI-1640 medium, MEM medium, or a serum-free medium, under common culture conditions (e.g., 37° C., 5% $CO_2$) for 2 to 10 days, and the antibody is obtained from the culture supernatant. In the case of the ascites development, about 10 millions of myeloma-derived hybridoma cells are administered intraperitoneally to an animal of the same species as the mammal from which the myeloma cell is derived, so as to allow the hybridoma cells to grow in a large quantity. After one to two weeks, the ascites or blood serum is collected from said animal.

Where the purification of an antibody is required in the above-described method for collecting the antibody, the conventional techniques, such as salting out by ammonium sulfate, ion-exchange chromatography, affinity chromatography, and gel chromatography, may be appropriately selected or combined to obtain the purified monoclonal antibody of the present invention.

The monoclonal antibody of the present invention includes a chimeric antibody such as a humanized mouse monoclonal antibody. The present invention also provides antigen-binding fragments of the aforementioned antibody. Examples of antigen-binding fragments that can be produced by a conventional technique include, but are not limited to, Fab and F(ab')$_2$ fragments. The present invention also provides antibody fragments and derivatives thereof that can be produced by genetic engineering. The antibody of the present invention can be used in vitro and in vivo for the assay that is intended to detect the presence of the polypeptide of the present invention or a (poly)peptide fragment thereof. The antibody of the present invention can be used for purifying a protein or a fragment thereof by immunoaffinity chromatography.

Preparation of Polyclonal Antibody:

When polyclonal antibodies are prepared, an animal is immunized in the same manner as described above, the antibody titer is measured 6 to 60 days after the final immunization by enzyme immunoassay (EIA or ELISA) or radio immunoassay (RIA), and blood is taken on the day the maximal antibody titer is measured, in order to obtain antiserum. Thereafter, the reactivity of the polyclonal antibodies in the antiserum is assayed by ELISA or the like.

Detection Method:

In the present invention, either an assay method involving the use of the antibody of the present invention, i.e., immunoassay, or a method for measuring the expression level of the gene encoding the CXCL1 protein, is preferably employed.

Examples of immunological assay techniques include enzyme immunoassay (ELISA or EIA), fluorescence immunoassay, radio immunoassay (RIA), luminescent immunoassay, immunonephelometry, latex agglutination assay, latex turbidimetry, hemagglutination, particle agglutination, and Western blotting.

Examples of the methods for assaying the expression levels of nucleic acids derived from the genes include quantitative RT-PCR, DNA array analysis, Northern blotting, Northern hybridization, Southern blotting, and Southern hybridization.

Samples to be analyzed in the method for detecting a protein of the present invention are not particularly limited, provided that such samples are biological samples that may contain the CXCL1 protein derived from urothelial cancer or nucleic acids derived from the gene encoding the protein. In particular, the determined values of the CXCL1 protein obtained from body fluid samples, such as urine, blood, blood plasma, or blood serum, are useful as an indication for urothelial cancer. The method for detecting urothelial cancer of the present invention is capable of detecting urothelial cancer not only in cancer tissue but also in blood or urine. Accordingly, this method is very useful as a simple detection method.

When the method for detecting a protein of the present invention is carried out by an immunoassay technique using a label, such as enzyme immunoassay, fluorescence immunoassay, radio immunoassay, or luminescent immunoassay, the antibody of the present invention may be immobilized, or a component in the sample may be immobilized to subject such substance to an immunological reaction.

Examples of solid-phase supports that can be used include insoluble supports in the form of beads, microplate, test tube, stick, or specimen (test strip) comprising a polystyrene, polycarbonate, polyvinyltoluene, polypropyrene, polyethylene, polyvinyl chloride, nylon, polymethacrylate, latex, gelatin, agarose, cellulose, sepharose, glass, metal, ceramic, or magnetic material.

The samples can be immobilized on the support in accordance with a conventional technique by binding the antibody of the present invention or a sample component to the solid-phase support by physical adsorption, chemical binding, or a combination thereof.

The present invention is intended to easily detect the reaction between the antibody of the present invention and the CXCL1 protein derived from the urothelial cancer cell in the sample. To this end, the antibody of the present invention is labeled to directly detect the reaction of interest. Alternatively, a labeled secondary antibody is used to indirectly detect the reaction. In the method of detection according to the present invention, the latter indirect detection technique (e.g., the sandwich technique) is preferably employed from the viewpoint of sensitivity.

Examples of label substances that can be used for enzyme immunoassay include peroxidase (POD), alkaline phosphatase, β-galactosidase, urease, catalase, glucose oxidase, lactate dehydrogenase, amylase, and a biotin-avidin complex. Examples of label substances that can be used for fluorescence immunoassay include fluorescein isothiocyanate, tetramethylrhodamine isothiocyanate, substituted rhodamine isothiocyanate, dichlorotriazine isothiocyanate, Alexa, and AlexaFluoro. Examples of label substances that can be used for radio immunoassay include tritium, iodine 125, and iodine 131. Examples of label substances that can be used for luminescent immunoassay include an NADH-, FMNH2-, luciferase system, luminol-hydrogen peroxide-POD system, acridinium ester system, or dioxetane compound system.

A label can be bound to the antibody in case of enzyme immunoassay, for example, by the glutaraldehyde method, the maleimide method, the pyridyl disulfide method, or the periodic acid method. Radio immunoassay can be carried out in accordance with conventional techniques, such as the chloramine-T method and Bolton-Hunter method. Such assay techniques can be carried out in accordance with conventional techniques (Current protocols in Protein Sciences, 1995, John Wiley & Sons Inc., Current protocols in Immunology, 2001, John Wiley & Sons Inc.). When the antibody of the present invention is directly labeled, for example, a component in the sample is immobilized and brought into contact with the labeled antibody of the present invention to form a complex of the CXCL1 protein and the antibody of the present invention. The unbound labeled antibody is separated by washing, and the amount of the CXCL1 protein in the sample can be determined based on the amount of the bound labeled antibody or the unbound labeled antibody.

When the labeled secondary antibody is used, for example, the antibody of the present invention is allowed to react with the sample (the primary reaction), then with the labeled secondary antibody (the secondary reaction). The primary reaction and the secondary reaction may be carried out in the reverse order, concurrently, or separately. The primary and secondary reactions result in the formation of a complex of immobilized CXCL1 protein/the antibody of the invention/the labeled secondary antibody or a complex of the immobilized antibody of the invention/CXCL1 protein/labeled secondary antibody. The unbound labeled secondary antibody is separated by washing, and the amount of the CXCL1 protein in the sample can be determined based on the amount of the bound labeled secondary antibody or of the unbound labeled secondary antibody.

In the enzyme immunoassay, specifically, the enzyme label is allowed to react with a substrate under optimal conditions, and the amount of the reaction product is assayed by an optical method or the like. In the fluorescence immunoassay, the fluorescent intensity from a fluorescent label is assayed. In the radio immunoassay, the radioactivity from radioactive label is assayed. In the luminescent immunoassay, the luminescent level from a luminescent reaction system is assayed.

In the method of the present invention, the generation of immune-complex aggregates in immunonephelometry, latex agglutination assay, latex turbidimetry, hemagglutination, particle agglutination, or the like is assayed by optically measuring the transmitted beam or scattered beam. When visually assayed, a solvent, such as a phosphate, glycine, Tris, or Good's buffer, can be used. Further, a reaction accelerator like polyethylene glycol or an inhibitor of nonspecific reaction may be added to the reaction system.

Hereafter, a preferable embodiment of the method of detection according to the present invention is described.

At the outset, the antibody of the present invention is immobilized on an insoluble support as a primary antibody. Preferably, the surface of the solid-phase support on which an antigen is not adsorbed is blocked with a protein that is not associated with the antigen (e.g., fetal calf serum, bovine serum albumin, or gelatin). Subsequently, the immobilized primary antibody is allowed to react with the analyte sample. The sample is then allowed to react with the labeled secondary antibody that reacts with the CXCL1 protein at a site different from the site of the reaction with the primary antibody to detect a signal from the label. The "the secondary antibody that reacts with the CXCL1 protein at a site different from the site of the reaction with the primary antibody" used herein is not particularly limited, provided that such antibody recognizes a site other than the site at which the primary antibody is bound to the CXCL1 protein. Such antibody may be a polyclonal, antiserum, or monoclonal antibody regardless of the type of immunogen. A fragment of such antibody, such as Fab, F(ab')$_2$, Fab, Fv, or ScFv, can also be used. Further, a plurality of types of monoclonal antibodies may be used as the secondary antibodies.

In contrast, the antibody of the present invention may be labeled to prepare a secondary antibody. At a site different from that for the antibody of the present invention, an antibody that reacts with the CXCL1 protein may be immobilized on an insoluble support as a primary antibody, and the immobilized primary antibody may be brought into contact with the analyte sample. The resultant may then be brought into contact with the antibody of the present invention that has been labeled as the secondary antibody to detect a signal from the aforementioned label.

As described above, the antibody of the present invention can react specifically with the CXCL1 protein derived from the urothelial cancer cell. Thus, the antibody of the present invention can be used as a diagnostic agent for cancer. The diagnostic agent of the present invention comprises the antibody of the present invention. Accordingly, the diagnostic agent of the present invention may be used to detect the CXCL1 protein derived from the urothelial cancer cell contained in the sample obtained from a subject who is suspected of having urothelial cancer. Thus, whether or not the subject suffers from a urothelial cancer can be determined.

The diagnostic agent of the present invention can be used for any means, provided that such means is for immunological assay. Use of the diagnostic agent of the present invention in combination with a simple means such as a test strip for immunochromatography known in the art enables diagnosis of cancer in a more simple and rapid manner. A test strip for immunochromatography is composed of, for example, a sample receiving portion comprising a material that easily absorbs the sample, a reagent portion comprising the diagnostic agent of the present invention, a development portion where the reaction product of the sample and the diagnostic agent migrates, a label portion where the developed reaction product is colored, and a presentation portion toward which the colored reaction product develops. Such test strip can be in the shape similar to that of a pregnancy test. First, the sample is applied to the sample receiving portion, and the sample receiving portion then absorbs and delivers the sample to the reagent portion. Subsequently, the reaction takes place between the CXCL1 protein derived from urothelial cancer cell in the sample and the antibody of the present invention at the reagent portion, the resulting composite migrates on the development portion to the label portion. The reaction between the resulting composite and the labeled secondary antibody takes place at the label portion, the reaction product with the labeled secondary antibody develops to the presentation portion, and color is then recognized. The aforementioned test strip for immunochromatography would not impart any pain or risk resulting from the use of the reagent to the user. Accordingly, such test strip can be used for at-home monitoring, and the results thereof can be subjected to thorough examination, and the subject of the monitoring can be subjected to treatment (e.g., surgical extirpation), at relevant medical institution, which can lead to the prevention of metastasis and/or recurrence. At present, such test strips can be mass-produced in a cost effective manner by the method described in, for example, JP Patent Publication (kokai) No. 10-54830 (1998) (A). Also, the use of the diagnostic agent of the present invention in combination with a diagnostic agent for an existing urothelial cancer tumor marker enables more reliable diagnosis.

Accordingly, the present invention relates to a kit for diagnosing the urothelial cancer comprising an antibody that reacts specifically with the CXCL1 protein or a fragment thereof or a fragment of such antibody. The antibody included in the kit of the present invention may be bound to a solid-phase support as described above. Further, the kit of the present invention can comprise, for example, a labeled secondary antibody, a support, a washing buffer, a sample diluent, a enzyme substrate, a reaction terminator, and the CXCL1 protein as a purified label substance.

Hereafter, the present invention will be described in greater detail with reference to the examples, although the technical scope of the present invention is not limited thereto.

EXAMPLES

(1) Proteome Analysis of Culture Supernatant of Normal Urothelial Cells

Normal urothelial cells were obtained from the normal urinary ducts of nephrectomy patients. The urothelial cells extracted from the normal urinary ducts were cultured in Defined KSFM medium in 10-cm culture dishes (Scriven, S. D. et al., 1997, Journal of Urology, vol. 158, pp. 1147-1152). When the urothelial cells that had been cultured in four 10-cm culture dishes reached 90% confluence, the cells were washed three times with PBS(-), the medium was exchanged with serum-free RPMI 1640 medium, culture was conducted for 24 hours, and the culture supernatant was collected. The resulting culture supernatant was subjected to ultracentrifugation at 150,000 g and 4° C. for 30 minutes to remove the sediment, the centrifugation supernatant was concentrated by centrifugation at 4,000 g and 4° C. for 20 minutes using the Amicon Ultra-15 (Millipore). As a result, 1 mg of protein was extracted from 40 ml of the culture supernatant.

The extracted proteins (200 μg) were divided into 26 fractions by reversed-phase chromatography using the ProteomeLab™ PF2D System (Beckman Coulter), digested with trypsin, and then subjected to exhaustive protein identification using the Q-TOF Ultima (Micromass). As a result, approximately 600 proteins were identified, approximately 20 of which were presumed to have growth factor activities.

(2) Analysis of Expressed Genes

The established bladder cancer cells (RT112, 5637, T24, and EJ) were cultured in 10% fetal calf serum-containing RPMI 1640 medium while the normal urothelial cells in Defined-KSFM. Total RNAs were prepared from these cells using the Trizol reagent (Invitrogen) and the RNeasy Mini kit (Qiagen) in accordance with the recommended protocols. cDNAs were synthesized from 3 μg of total RNA using the First-Strand cDNA synthesis kit (Amersham Biosciences). The cDNAs were used as templates, primers for a growth factor discovered as a result of proteome analysis, i.e., CXCL1, and a receptor thereof, i.e., CXCR2, were designed, gene expression was analyzed by RT-PCR, and the presence or absence of the expression was confirmed by agarose gel electrophoresis using the molecular weight as an indication (FIG. 1). The Hi-Lo DNA Marker (BIONEXUS) was used as a molecular weight marker.

The expression level of CXCL1 mRNA was high in the 5637 and T24 cell lines derived from infiltrative bladder cancer. Although the expression was observed in normal cells, the degree of expression was found to be lower than the expression level in the cell lines derived from infiltrative cancer.

(3) Determining CXCL1 Concentration in Culture Supernatant

Figure 2:
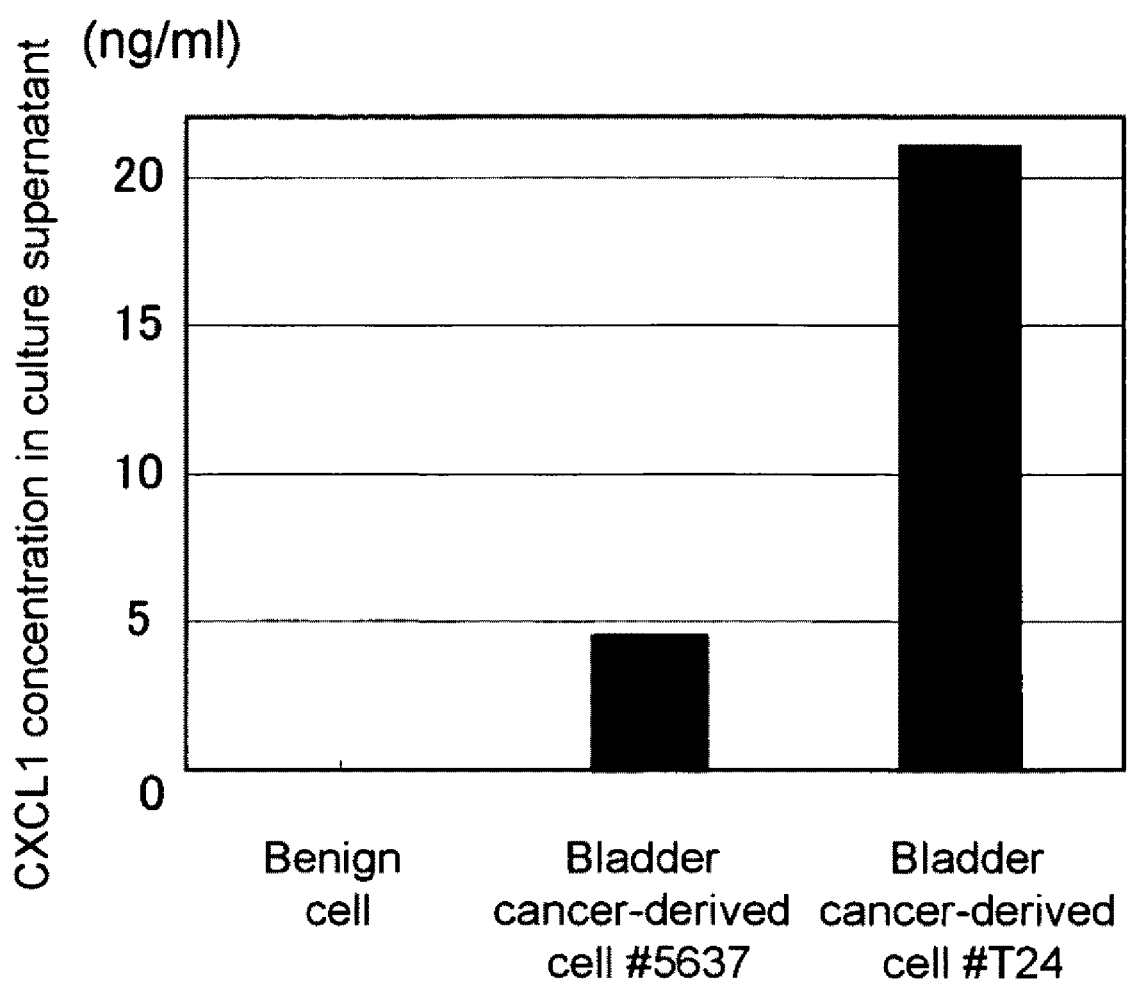
FIG. 2 shows the expression levels of the CXCL1 proteins in the culture supernatants of the established bladder cancer cells and of the normal urothelial cells.

The established bladder cancer cell lines (5637 and T24) were cultured in 10% fetal calf serum-containing RPMI 1640 medium while the normal urothelial cells in Defined-KSFM. The cells were cultured on a 96-well plate for 24 hours, and the culture medium was exchanged when culture confluence was substantially attained. The culture supernatant was recovered 24 hours thereafter. The concentration of the CXCL1 protein in the culture supernatant was determined using the Human GRO alpha/CXCL1 Quantikine ELISA kit (R&D Systems). As a result, CXCL1 was not detected in the culture supernatant of normal urothelial cells, whereas the CXCL1 was detected in the culture supernatants of 5637 and T24 cell lines derived from infiltrative cancer, at a high concentration over about 5-20 ng/ml (FIG. 2).

(4) Determining CXCL1 Concentration in Urine of Bladder Cancer Patient

Figure 3:
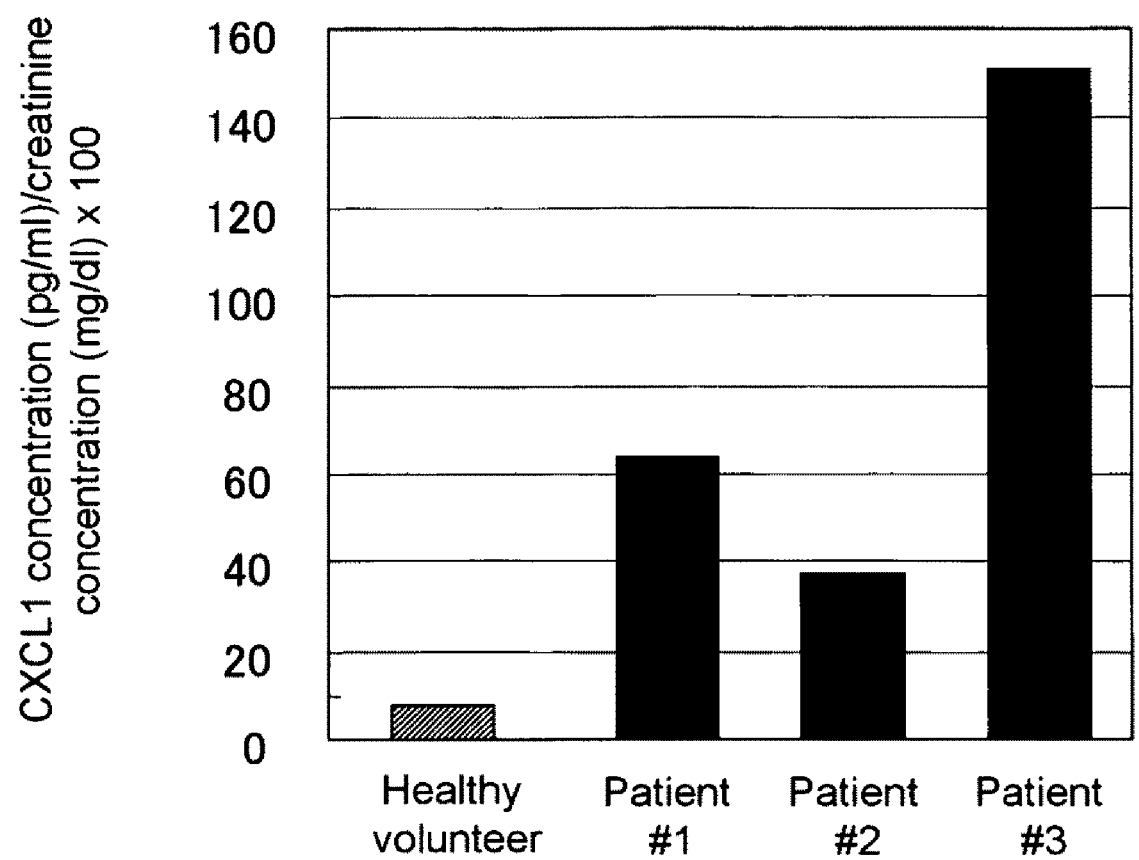
FIG. 3 shows the CXCL1 protein expression in the urine of bladder cancer patients.

Urine samples were obtained from 3 patients with infiltrative bladder cancer and one (1) healthy volunteer, and the CXCL1 protein concentration in the urine was determined using the Human GRO alpha/CXCL1 Quantikine ELISA kit (R&D Systems). The CXCL1 protein concentration Was corrected using the urine creatinine concentration in the samples, and the urine CXCL1 protein concentration was found to be higher in the bladder cancer patients than a healthy volunteer (FIG. 3).

Figure 4:
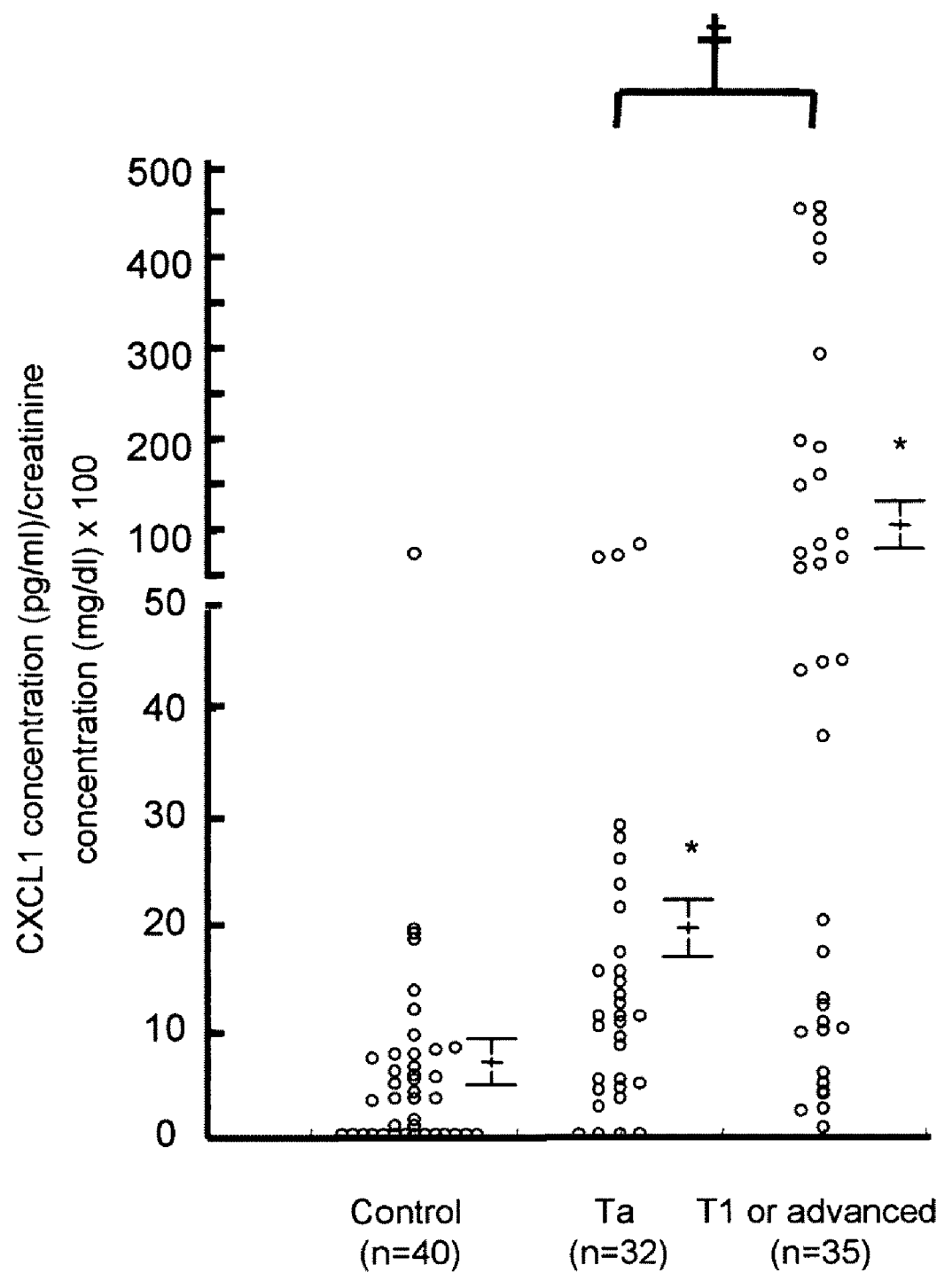
FIG. 4 shows the results of assaying the expression levels of CXCL1 proteins in the urine of bladder cancer patients, wherein open circles indicate numerical values from the data, and the means and the standard deviations are indicated with "+"; * indicates a risk of $p<0.001$, indicating a significant difference between the healthy volunteers (control samples) and patients with early-stage cancer (Ta); and + indicates a risk of $p<0.01$, indicating a significant difference between patients with early-stage cancer and patients with progressive cancer (T1 or advanced).

(5) Determining CXCL1 Concentration in Urine of Bladder Cancer Patient in Accordance with the Stage of Progression Urine samples were obtained from 32 patients of early-stage (Ta) bladder cancer, 35 patients of progressive (T1 or advanced) bladder cancer, and 40 healthy volunteers, and the CXCL1 protein concentrations in the urine samples were determined using the Human GRO alpha/CXCL1 Quantikine ELISA kit (R&D Systems). The urine CXCL1 protein concentration levels were found to be higher in the early-stage and progressive bladder cancer patients than healthy volunteers (FIG. 4).

(6) Assay of CXCL1 Expression in Normal Urothelial Tissue and in Bladder Cancer Tissue Normal urothelial tissue and urothelial cancer tissue were individually immobilized with 10% neutral formalin and then embedded in paraffin. The paraffin block was cut into 5-μm-thick sections subjected to deparaffinization and moistening, and then immobilized on glass slides. The endogenous peroxidase activity was inhibited by hydrogen peroxide. The glass slides were washed with PBS and then treated with PBS containing 1% rabbit serum for 30 minutes. The anti-CXCL1 antibody (Groα (C-15):SC1374, Santa Cruz Biotechnology) was diluted to 1:150 to prepare a primary antibody and then allowed to stand at 4° C. overnight. Further, Histofine® Simple Stain MAX PO (Nichirei Biosciences Inc., Japan) was used to develop color with the aid of diaminobenzidine. Further, the sections were slightly stained with hematoxylin. When 10% or more of the cytoplasm of the tumor cells were stained, the cells were determined to be CXCL1-positive cells.

Figure 5:
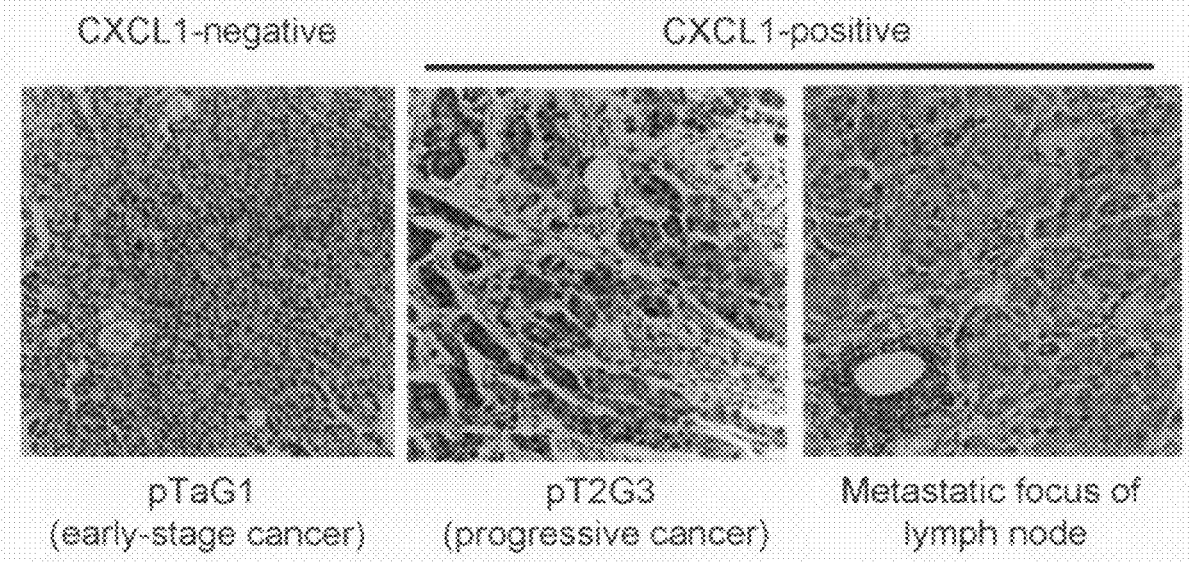
FIG. 5 is a diagram showing the results of immunostaining the CXCL1 protein expressed in the tissue of a bladder cancer patient. The level of staining was high in the progressive (pT2G3) cancer tissue and in the metastatic focus of lymph node; however, staining was not observed in normal urothelial tissue (pTaG1).

Normal urothelial cells were not stained and CXCL1 expression was not observed therein. In progressive (pT2G3) bladder cancer tissue and in metastatic focus of lymph node, strong staining was observed, which indicates strong expression of CXCL1 (FIG. 5).

According to the present invention, therefore, the expression or the expression level of the CXCL1 gene in urothelial tissue or cells may be determined and compared with the controls with the use of the aforementioned antibody or nucleic acid probe. Thus, a urothelial cancer, such as early-stage or progressive bladder cancer, can be effectively detected by detection of the expression of the gene of interest or by using the increase in expression level of the gene as the indication

INDUSTRIAL APPLICABILITY

The present invention makes the effective detection of a urothelial cancer possible in a simple and cost-effective manner, which enables early detection, diagnosis, and treatment of a urothelial cancer. Because the urothelial cancer can be detected in a non-invasive manner by the method of the present invention using urines from patients, the method provides a simple and rapid detection method.

All publications, patents, and patent applications cited herein are incorporated herein by reference in their entirety.

The invention claimed is:

1. A method for detecting or diagnosing an urothelial cancer comprising:
   (a) measuring the amount of CXCL1 protein, or the transcription product level of a gene encoding the protein, in vitro in a biological sample selected from urine or an urothelial tissue or cell from a subject,
   (b) comparing to a control sample the amount of CXCL1 protein or the transcription product level of a gene encoding the protein in the biological sample; and
   (c) classifying the subject as having an urothelial cancer based on an increase in the amount of the protein or in the transcription product level of the gene relative to that of a control sample, and wherein in the case that the biological sample is an urothelial tissue or cell, the increase is more than 3 times.

2. The method according to claim 1, wherein the increase is at least 2 times.

3. The method according to claim 1, wherein the increase is at least 3 times.

4. The method according to claim 1, wherein the measurement is carried out by an immunological method.

5. The method according to claim 1, wherein the measurement is carried out by hybridization.

6. The method according to claim 1, wherein the measurement is carried out with the use of a substance capable of binding to the protein or a transcription product of the CXCL1 gene.

7. The method according to claim 6, wherein the substance capable of binding to the protein is an antibody or a fragment thereof.

8. The method according to claim 6, wherein the substance capable of binding to the gene is a nucleic acid probe.

9. The method according to claim 8, wherein the nucleic acid probe comprises a nucleic acid consisting of the nucleotide sequence as shown in SEQ ID NO: 1 or a mutant thereof, a nucleic acid consisting of a sequence complementary thereto, a nucleic acid hybridizing under stringent conditions to the nucleic acid, or a fragment comprising 15 or more continuous nucleotides thereof.

10. The method according to claim 7, wherein the antibody is labeled.

11. The method according to claim 1, wherein the protein is measured immunologically in a sample using an antibody or fragment thereof, which binds specifically to the protein or a fragment thereof.

12. The method according to claim 1, wherein the expression level of the gene is measured in the sample using a probe, which is a nucleic acid consisting of the nucleotide sequence as shown in SEQ ID NO: 1 or a mutant thereof, a nucleic acid consisting of a sequence complementary thereto, a nucleic acid hybridizing under stringent conditions to the nucleic acid, or a fragment comprising 15 or more continuous nucleotides thereof, thereby detecting a urothelial cancer using, as an indication, the increase in expression level of the gene relative to that of a control sample.

13. The method according to claim 1, wherein the urothelial cancer is selected from the group consisting of bladder cancer, renal pelvis cancer, urinary duct cancer, and urinary tract cancer.

14. The method according to claim 1, wherein the sample is urine.

15. The method according to claim 1, wherein the sample is an urothelial tissue or cell.

16. The method according to claim 1, wherein the protein has the amino acid sequence as shown in SEQ ID NO: 2 or a mutant thereof.

17. The method according to claim 1, wherein the gene has the nucleotide sequence as shown in SEQ ID NO: 1 or a mutant thereof.

* * * * *